United States Patent [19]

Sung et al.

[11] 4,257,779

[45] Mar. 24, 1981

[54] HYDROCARBYLSUCCINIC ANHYDRIDE AND AMINOTRIAZOLE REACTION PRODUCT ADDITIVE FOR FUEL AND MINERAL OILS

[75] Inventors: Rodney L. Sung; William P. Cullen, both of Fishkill; Peter Dorn, Lagrangeville, all of N.Y.

[73] Assignee: Texaco Inc., White Plains, N.Y.

[21] Appl. No.: 753,963

[22] Filed: Dec. 23, 1976

[51] Int. Cl.$^3$ .............................................. C10L 1/22
[52] U.S. Cl. .................................... 44/63; 252/51.5 A
[58] Field of Search ................ 44/63, 71; 252/51.5 A; 260/308 R

[56] References Cited

U.S. PATENT DOCUMENTS

| 3,219,666 | 11/1965 | Norman et al. | 260/308 R |
| 3,272,746 | 9/1966 | Le Suer et al. | 260/308 R |

Primary Examiner—Winston A. Douglas
Assistant Examiner—Y. Harris-Smith
Attorney, Agent, or Firm—Carl G. Ries; Robert A. Kulason; James J. O'Loughlin

[57] ABSTRACT

A hydrocarbylsuccinic anhydride and aminotriazole reaction product having detergent properties for fuels and lubricants is provided.

7 Claims, No Drawings

HYDROCARBYLSUCCINIC ANHYDRIDE AND AMINOTRIAZOLE REACTION PRODUCT ADDITIVE FOR FUEL AND MINERAL OILS

BACKGROUND OF THE INVENTION

1. Field of the Invention

Internal combustion gasoline engine design is undergoing important changes to meet stricter standards set for engine and exhaust gas emissions. One major change in engine design is the feeding of blow-by gases from the crankcase zone of the engine into the intake air-fuel mixture at the carburetor just below the throttle plate, rather than venting these gases to the atmosphere as was the practice formerly. These blow-by gases contain substantial amounts of deposit forming substances and are known to form deposits in and around the throttle plate area of the carburetor. Another significant change in engine design and operation is the recirculation of a part of the exhaust gases to the fuel air intake of the engine. These exhaust gases also have pronounced deposit forming tendencies. The carburetor deposits produced by the recirculated blow-by and exhaust gases restrict the flow of air through the carburetor at idle and at low speeds so that an overrich fuel mixture results. This condition produces rough engine idling and/or stalling and leads to the release of excessive hydrocarbon exhaust emissions to the atmosphere.

Many detergent additives for motor fuel compositions are known in the art and are eminently effective for this purpose. There is, however, a major drawback associated with the use of many of the known carburetor detergents including materials which are outstanding carburetor detergents. The problem referred to is the octane requirement increase of the engine brought about as a result of the use of the carburetor detergent. While not fully understood, many carburetor detergents cause an octane requirement increase in the engine of 3 or 4 or more octane units as measured by the Research Octane Number method. This phenomenon is believed to be due to an increase in deposits formation in the combustion zone of the engine leading to a higher than design compression ratio in the engine and a higher octane requirement. This is a very serious problem when viewed from its impact on the comsumption of high octane gasoline with its reduced volumetric yield from the basic petroleum resource.

The detergent additive is also useful in diesel oils, fuel oils, engine oils and in mineral lubricating oil compositions.

2. The Prior Art

Detergent oil compositions are disclosed in U.S. Pat. Nos. 3,275,554; 3,676,089; 3,905,781 and 3,927,104.

A copending application Ser. No. 753,962 filed Dec. 23, 1976, now abandoned in favor of a continuation, Ser. No. 940,928, filed Sept. 11, 1978 is directed to the additive reaction product of a hydrocarbylsuccinic anhydride in which the hydrocarbyl radical has from about 6 to 30 carbon atoms and to rust-inhibited oil compositions containing the additive.

SUMMARY OF THE INVENTION

An oil-soluble, ashless detergent for a mineral oil composition comprising the reaction product of a hydrocarbyl succinic anhydride in which the hydrocarbyl radical has from 60 to 200 carbon atoms and an aminotriazole is provided as well as hydrocarbon derived fuel and lubricating oil compositions containing the reaction product.

SPECIFIC EMBODIMENTS OF THE INVENTION

The reaction product of the invention is obtained by reacting a hydrocarbyl-substituted succinic anhydride with an aminotriazole at a temperature ranging from about room temperature to about 150° C. until the substantial completion of the reaction. This reaction is conducted in the absence of any catalyst but generally in the presence of a solvent to facilitate the reaction.

The hydrocarbyl-substituted succinic anhydride reactant is represented by the formula:

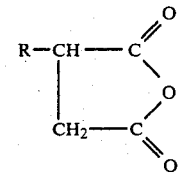

in which R is a monovalent aliphatic hydrocarbon radical having at least 60 carbon atoms ranging up to about 200 carbon atoms. A preferred hydrocarbyl-substituted succinic anhydride reactant is one in which the hydrocarbyl radical has from about 80 to 170 carbon atoms with the particularly preferred compounds being those in which the hydrocarbyl radical has from 90 to 120 carbon atoms.

The hydrocarbyl or aliphatic hydrocarbon radical can be a straight or branched-chain hydrocarbyl radical and can be saturated or unsaturated.

The aminotriazole reactant is represented by the following formula:

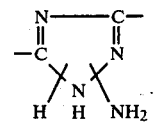

It will be understood that the hydrogen and the amino radicals are attached at the unsatisfied carbon atom bonds and that they can be interchanged in these positions.

Suitable amino-triazoles include 3-amino-1,2,4-triazole and 5-amino-1,2,4-triazole.

The hydrocarbon-substituted succinic anhydride and the aminotriazole are reacted in the proportion of from about 0.5 to 1.5 moles of said aminotriazole per mole of said hydrocarbon-substituted succinic anhydride. A preferred mole ratio for preparing the reaction product is from about 0.8 to 1.2 moles of said aminotriazole per mole of said hydrocarbon-substituted succinic anhydride. It is most preferred, however, to prepare the reaction product by reacting approximately equimolar amounts of the hydrocarbon-substituted succinic anhydride with the aminotriazole. Effective detergents will result when the reactants are reacted within the broad proportions prescribed. However, the most effective detergent results when essentially equal mole proportions of the reactants are employed.

The reaction is facilitated by the use of a solvent for the reactants which is inert to the reactants and to the reaction product. A broad range of inert organic aromatic and aliphatic solvents are suitable for this purpose. In general, the aliphatic and aromatic hydrocarbon having from about 6 to 10 carbon atoms are especially suitable including such solvents as benzene, toluene, pentane, hexane, and heptane.

This reaction is readily conducted at a temperature ranging from about room temperature up to about 150° C. with the preferred reaction temperature being from about 50° to 100° C. Higher and lower temperatures can be employed but generally at the expense of economy and efficiency. In practice, it is convenient to conduct the reaction at about the reflux temperature of the solvent which has been selected for the reaction.

The following examples illustrate the preparation of the reaction product of the invention.

EXAMPLE I 295 grams (0.22 mole) of polyisobutenylsuccinic anhydride in which the polyisobutenyl radical has a molecular weight of 1320 and 21 grams (0.25 mole) of 3-aminotriazole are dissolved in 50 milliliters of benzene. The temperature of the mixture is raised to the reflux temperature of benzene and the mixture is refluxed for about 8 hours. The mixture containing the reaction product is filtered and the benzene is removed by distillation under a vacuum.

The reaction product recovered contains 3.39% nitrogen. Infrared spectroscopy indicates that the product has the structure:

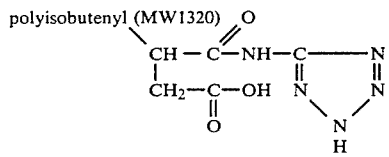

EXAMPLE II 460 grams (0.21 mole) of polyisobutenylsuccinic anhydride in which the polyisobutenyl radical has a molecular weight of 2060 and 21 grams (0.25 mole) of 3-aminotriazole are dissolved in 100 milliliters of benzene. The temperature of the reaction mixture is raised to the reflux temperature of benzene and refluxed for about 8 hours. The solution containing the reaction product is filtered, the benzene is removed by distillation and a product is obtained similar to the product of Example I.

EXAMPLE III 431.6 grams (0.2 mole) of polyisobutenylsuccinic anhydride in which the polyisobutenyl radical has a molecular weight of 920 and 21 g (0.25 mole) of 3-aminotriazole are dissolved in 100 ml of benzene. The mixture is refluxed for 8 hours. The reaction mixture is filtered, the benzene is stripped off under vacuum and a product is obtained similar to the product of Example I.

EXAMPLE IV 479.6 g (0.2 mole) of polyisobutenylsuccinic anhydride in which the polyisobutenyl radical has a molecular weight of 2300 and 21 g (0.25 mole) of 3-aminotriazole are dissolved in 100 ml of benzene. The mixture is refluxed for about 8 hours. The reaction mixture is filtered, benzene is stripped off under vacuum and a product is obtained similar to the product of Example I.

EXAMPLE V 169 grams (0.2 mole) polyisobutenylsuccinic anhydride in which the polyisobutenyl radical has a molecular weight of 750 and 21 g (0.25 mole) 3-aminotriazole are dissolved in 50 ml of benzene. This mixture is reacted at the reflux temperature of benzene for about 8 hours. The reaction mixture is filtered, the benzene is stripped off in vacuo and a product is obtained similar to the product of Example I.

EXAMPLE VI 189.6 g (0.2 mole) polypropenyl succinic anhydride in which the polypropenyl radical has a molecular weight of about 800–900 and 21 g (0.25 mole) of 3-aminotriazole are dissolved in 50 ml benzene. The mixture is refluxed for 8 hours. The reaction mixture is filtered, and the benzene is stripped in vacuo. A product is obtained similar to the product of Example I.

The novel detergent additive of the invention is effective in a gasoline or motor fuel composition. The base fuel for a motor fuel composition consists of a mixture of hydrocarbons boiling in the gasoline boiling range generally from about 90° to 450° F. This base fuel may consist of straight-chain or branched paraffins, cycloparaffins, olefins, and aromatic hydrocarbons and any mixture of these. The base fuel can be derived from straight-run naphtha, polymer gasoline, natural gasoline or from catalytically cracked or thermally cracked hydrocarbons and catalytically reformed stocks. The hydrocarbon composition and the octane level of the base fuel are not critical. Any conventional motor fuel base may be employed in the practice of this invention.

The detergent additive can also be effectively employed in an oil of lubricating viscosity. This oil substrate may be a mineral, a synthetic or a mixed mineral-synthetic lubricating oil. Suitable synthetic oil substrates include ester base oils, alkylene polymers, alkylene epoxide type polymers, alkyl benzenes, polyphenyls and the like. The preferred oil substrate is a hydrocarbon mineral oil. This oil can be a paraffin base, naphthenate base, or mixed paraffin-naphthenate-base lubricant composition. The lubricating oil base will generally have been subjected to solvent refining to improve its lubricity and viscosity temperature relationship as well as solvent dewaxing to remove waxy components and improve the pour of the oil. Generally, mineral lubricating oils having an SUS viscosity at 100° F. between about 100 and 600 may be used in the formulation of the improved lubricants of this invention.

The novel detergent is useful in a lubricating oil composition in a concentration ranging from about 0.05 to 5 percent by weight of the lubricating oil composition. For convenience of handling and storing, solutions or concentrates of the detergent additive can be prepared containing from about 0.05 to 50 weight percent of the additive in a lubricating oil or a mineral oil substrate.

In general, the additive of the invention is added to a motor fuel composition in a minor amount, i.e. an amount effective to provide detergency to the gasoline. The additive is effective as a detergent in a motor fuel composition in amounts ranging from about 0.001 to 0.25 weight percent based on the total fuel composition. It is preferred, however, to employ concentrations ranging from about 0.02 to 0.10 weight percent in gasoline.

A motor fuel composition according to the invention will generally contain any of the additives normally employed in a motor fuel. For example, the base fuel may be blended with an anti-knock compound, such as a tetraalkyl lead compound, including tetraethyl lead (TEL), tetramethyl lead, tetrabutyl lead, and chemical and physical mixtures thereof or cyclopentadienyl manganese tricarbonyl type compounds generally in a concentration from about 0.05 to 4.0 cc per gallon of gasoline. The motor fuel composition may also be fortified with any of the known conventional additives including anti-icing additives, corrosion inhibitors and the like.

A motor fuel composition containing the prescribed reaction product of the invention was tested for its effectiveness as a carburetor detergent in the Chevrolet Carburetor Detergency Test. The Base Fuel employed in these examples was a premium grade gasoline having a Research Octane Number of about 100 and contained 3 cc of tetraethyl lead per gallon. This gasoline consisted of about 22 percent aromatic hydrocarbons, 11 percent olefinic hydrocarbons and 67 percent paraffinic hydrocarbons and boiled in the range from about 90° to 370° F.

CHEVROLET CARBURETOR DETERGENCY TEST

This test is run on a Chevrolet V-8 Engine mounted on a test stand using a modified four-barrel carburetor. The two secondary barrels of the carburetor are sealed and the feed to each of the primary barrels arranged so that the separate fuels can be run in each barrel simultaneously. The primary carburetor barrels are also modified so that they have removable aluminum inserts in the throttle plate area in order that deposits formed on the inserts in this area can be conveniently weighed.

In the procedure designed to determine the effectiveness of an additive fuel to remove preformed deposits in the carburetor, the engine is run for a period of time, usually 24 to 48 hours, using the base fuel as the feed to both barrels with engine blow-by circulated to the air inlet of the carburetor. The weight of the deposits on both sleeves is determined and recorded. The engine is then cycled for 24 additional hours with a reference fuel being fed to one barrel, additive fuel to the other, and no blow-by to the carburetor air inlet. The inserts are then removed from the carburetor and weighed to determine the difference between the performance of the additive and the reference fuels in removing the preformed deposits. After the aluminum inserts are cleaned, they are replaced in the carburetor and the entire process repeated with the additive and reference fuels being reversed in the carburetor to minimize differences in fuel distribution and barrel construction.

The motor fuel used as a standard for comparison purposes in this test was a commercial high octane premium gasoline containing an effective carburetor detergent. The fuel composition representative of the invention consisted of the Base Fuel described above containing the indicated amount of the detergent additive of the invention. The results of this test are reported as the percent of preformed carburetor deposits removed by the novel additive containing gasoline of the invention in comparison to the deposits removed by the commercial detergent gasoline.

The results of the Chevrolet Carburetor Detergency Test are set forth in Table I below.

TABLE I

| CHEVROLET CARBURETOR DETERGENCY TEST | | |
|---|---|---|
| Run | Fuel | % Deposit Removed |
| 1. | Commercial Detergent Fuel[a] | 87 |
| 2. | Base Fuel + 100 PTB of Example 1 | 73 |

[a]This commercial fuel contained approximately 173 PTB of a carburetor detergent additive.

The foregoing tests demonstrate the outstanding carburetor detergency properties of the fuel composition of the invention. This novel fuel composition is especially suitable for maintaining carburetor cleanliness and, as a result, lower exhaust emissions in the operation of a modern internal combustion gasoline engine.

A motor fuel composition containing the prescribed reaction product of the invention was tested for its effect on the ORI or octane requirement increase in an engine. The Base Fuel employed in this was a premium grade gasoline essentially unleaded with less than 0.05 g of TEL per gallon having a Research Octane Number of about 91. This gasoline consisted of about 22 percent aromatic hydrocarbons, 11 percent olefinic hydrocarbons and 67 percent paraffinic hydrocarbons and boiled in the range from about 90° to 370° F.

The Octane Requirement Increase Test was run on a Waukesha RDH engine loaded by a craddled electric dynamometer. The base fuel employed was the unleaded gasoline described above. One run was conducted using the detergent additive of Example I of the invention in the unleaded gasoline at a concentration of 100 PTB (pounds of additive per 1000 barrels of gasoline). The second run was conducted using a commercial carburetor detergent additive.

The motor fuel containing the detergent additive of Example I of the invention gave the same ORI as the base fuel.

The motor fuel composition containing the commercial carburetor detergent additive gave an ORI that was 4 units higher than the base fuel.

These tests demonstrate that the carburetor detergent of the invention did not aggravate the Octane Requirement Increase of the engine and, in this regard, is a surprising improvement over the motor fuel with the commercial detergent additive fuel composition which caused a marked increse in the ORI of the engine.

We claim:
1. A fuel composition comprising a mixture of hydrocarbons boiling in the range from about 90° to 450° F. containing from about 0.01 to 0.25 weight percent of the reaction product of a hydrocarbylsuccinic anhydride and an aminotriazole, said reaction product being obtained by reacting from 0.5 to 1.5 moles of said aminotriazole per mole of said hydrocarbylsuccinic anhydride at a temperature in the range from about 20° to 150° C., said hydrocarbyl succinic anhydride being represented by the formula:

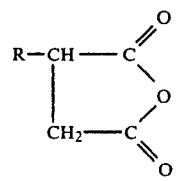

in which R is a monovalent aliphatic hydrocarbon radical having at least 60 carbon atoms and said aminotriazole is represented by the formula:

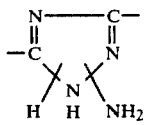

2. A composition according to claim 1, in which the hydrocarbyl radical in said hydrocarbylsuccinic anhydride has from 60 to 200 carbon atoms.

3. A composition according to claim 1, in which the hydrocarbyl radical in said hydrocarbylsuccinic anhydride has from about 80 to 170 carbon atoms.

4. A composition according to claim 1, in which the hydrocarbyl radical in said hydrocarbylsuccinic anhydride has from 90 to 120 carbon atoms.

5. A composition according to claim 1, in which said reaction product is obtained by reacting about 0.8 to 1.2 moles of said aminotriazole per mole of said hydrocarbylsuccinic anhydride.

6. A motor fuel composition according to claim 1, in which said reaction product is obtained by reacting approximately equimolar amounts of said reactants.

7. A motor fuel composition according to claim 1 in which said aminotriazole is 3-amino-1,2,4-triazole.

* * * * *